United States Patent
Ludescher et al.

(10) Patent No.: US 6,169,180 B1
(45) Date of Patent: *Jan. 2, 2001

(54) PROCESS FOR THE PRODUCTION OF CEPHALOSPORINES

(75) Inventors: Johannes Ludescher, Breitenbach; Hubert Sturm, Innsbruck; Josef Wieser, Kufstein, all of (AT)

(73) Assignee: Biochemie Gesellschaft, Tyrol (AT)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/947,215

(22) Filed: Oct. 8, 1997

Related U.S. Application Data

(62) Division of application No. 08/437,083, filed on May 5, 1995, now Pat. No. 5,686,604, which is a division of application No. 07/932,145, filed on Aug. 19, 1992, now abandoned.

(30) Foreign Application Priority Data

Aug. 19, 1992 (AT) ................................................. 07/932145

(51) Int. Cl.⁷ ....................... C07D 501/06; C07D 501/04
(52) U.S. Cl. .......................... 540/215; 540/222; 540/223; 540/226; 540/227
(58) Field of Search ............................................. 540/215

(56) References Cited

U.S. PATENT DOCUMENTS

| | | | |
|---|---|---|---|
| 4,112,087 | 9/1978 | Beeby | 424/246 |
| 4,139,618 | 2/1979 | Beeby | 424/246 |
| 4,358,588 | * 11/1982 | Henniger et al. | 544/30 |
| 4,640,798 | 2/1987 | Corfield et al. | 540/215 |
| 4,661,590 | 4/1987 | Hoshi et la. | 540/215 |
| 4,703,118 | 10/1987 | Lord et al. | 540/215 |
| 5,583,216 | * 12/1996 | Ochiai et al. | 540/222 |

FOREIGN PATENT DOCUMENTS

| | | |
|---|---|---|
| 3404615 | 8/1984 | (DE) . |
| 0315518 | 5/1989 | (EP) . |
| 0333154 | 9/1989 | (EP) . |

OTHER PUBLICATIONS

Kamachi, J. Antiobiotics, vol. 45, p. 533 (1990).
Derwent Abstract 88–106870/16 of EP 264–091–A, Apr. 20, 1988.
Derwent Abstract 85–26–4701/43 of DE 3512–225–A, Oct. 17, 1985.
Derwent Abstract 87–192428/27 of WO 8703875–A, Jul. 2, 1987.
Derwent Abstract 88–0728866/11 of GB 2194–790–A, Mar. 16, 1988.
Derwent Abstract 11146Y of BE–845167, Feb. 14, 1977.

* cited by examiner

Primary Examiner—John M. Ford

(57) ABSTRACT

The invention relates to a new economical and simple process, using a new intermediate compound, for the production of 3'-substituted 7-amino-3-propenyl-4-cephem-carboxylic acid derivatives of formula

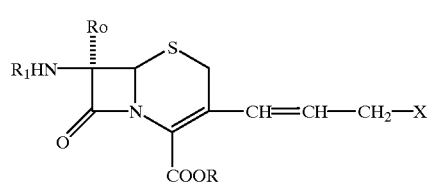

I wherein R is hydrogen, a negative charge or a silyl protecting group, $R_o$ is hydrogen or methoxy, $R_1$ is hydrogen or a silyl protecting group and X is the radical of a nucleophile, and their acid addition salts.

3 Claims, No Drawings

PROCESS FOR THE PRODUCTION OF CEPHALOSPORINES

This is a Division of application Ser. No. 08/437,083 filed May 5, 1995 now U.S. Pat. No. 5,686,604 which is a division of application Ser. No. 07/932,145 filed Aug. 19, 1992 (now abandoned).

The invention relates to a new economical and simple process, using a new intermediate compound, for the production of 3'-substituted 7-amino-3-propenyl-4-cephem-carboxylic acid derivatives of formula I

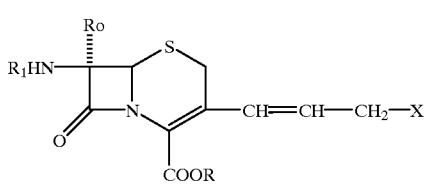

wherein R is hydrogen, a negative charge or a silyl protecting group, $R_o$ is hydrogen or methoxy, $R_1$ is hydrogen or a silyl protecting group and X is the radical of a nucleophile, and their acid addition salts.

Compounds of formula I are useful starting products for the production of valuable 3-substituted propenyl cephalosporines.

Illustrative examples of X are a) an unsaturated heterocyclic ammonium group of formula II

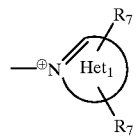

wherein $Het_1$ signifies a 5- or 6-membered heterocycle which optionally contain one or two additional heteroatoms selected from oxygen, nitrogen or sulphur atoms, $R_7$ is hydrogen, carboxy, carboxamido, a sulphonic acid radical or a substituent which is usual in β-lactam chemistry, e.g. alkoxy, hydroxy, acyl, amino, alkylthio mercapto, and wherein both the $R_7$ signify an optionally substituted, saturated or unsaturated alkyl group, or form part of an optionally substituted, saturated or unsaturated carbocyclic ring or part of a further (anellated) hetero-aromatic ring or b) an aliphatic ammonium group of formula III

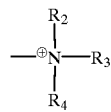

wherein $R_2$, $R_3$ and $R_4$ may be the same or different and respectively signify alkyl, alkenyl, aryl, hydroxy lower alkyl, carbamoyl lower alkyl, amino lower alkyl, acylamino lower alkyl, cyano lower alkyl or carboxy lower alkyl or $R_2$ with $R_3$ and the nitrogen atom signify a carbocyclic unsaturated ring which is alkyl-substituted by $R_4$, whereby $R_4$ may additionally represent a 1,3- or 1,4-alkylene or vinylene bridge or $R_2$ and $R_3$ and the nitrogen atom signify a carbocyclic saturated ring, wherein $R_4$ is a vinylene bridge, or c) a saturated heterocyclic ammonium group or d) a nitrogen base of formula IV

—NH—$R_5$  IV wherein $R_5$ signifies hydrogen or has the significance of $R_2$, or e) an optionally substituted tetrazole, triazole, imidazole, pyrrolidine or pyrazole, or f) an optionally substituted heterocyclic thiole radical of formula V

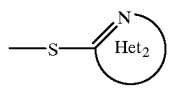

wherein $Het_2$ signifies a heterocycle or g) a thiole radical of formula VI

—S—$R_8$  VI wherein $R_8$ signifies an optionally substituted alkyl, alkenyl, aryl, acyl, carbamoyl, thiocarbamoyl or carbalkoxy radical or the thia-analogues thereof, or h) $N_3$.

Examples of group a) are optionally substituted thiazolium, pyrrolinium, thiadiazolium, oxadiazolium, oxazolium, pyridinium, thiazol[4,5-c]pyridinium, thieno [2,3-b]pyridinium, thieno[3,2-b]pyridinium, isoquinolinium or quinolinium.

Examples of group b) are tri(lower)alkylammonium, especially trimethylammonium, (1-carbamoyl-2-hydroxyethyl)dimethylammonium (carbamoylmethyl) (ethyl)-methylammonium, (cyanomethyl) dimethylammonium, (2-oxopropyl)dimethylammonium or dehydroquinuclidinium.

Examples of group c) are 1-methylpyrrolidinium, pyrrolidinium, piperidinium, 1-methylpiperidinium, 1-methylpiperazinium, 1-methylpyrazolidinium, 1,5-diazabicyclo[3.3.0]octan-1-ium, 1,4-diazabicylo[2.2.2] octan-1-ium, quinuclidinium or 1-aza-5-methyl-4,6-dioxabicyclo[3.3.1]nonan-1-ium.

Examples of group e) are 1,2,4-triazolyl, 1-methyl-1H-tetrazol-5-yl, 1-carboxymethyl-1H-tetrazol-5-yl or 1,2,3-triazol-5-yl.

The term heterocycle in the definition of $Het_2$ in group f) refers to a single ring or fused heterocyclic rings having 4 to 7, preferably 5- or 6- atoms in each ring, there being up to four hetero atoms in each ring selected from oxygen, nitrogen and sulphur in each ring, which heterocyclic ring may carry 1 to 3 optional substituents selected from ($C_{1-4}$)alkyl, ($C_{2-4}$)alkenyl, ($C_{1-4}$)alkoxy, halogen, trihalo-($C_{1-4}$)alkyl, hydroxy, acyloxy, oxo, mercapto, amino, carboxyl, carbamoyl, di-($C_{1-4}$)alkylamino, carboxymethyl, carbomoylmethyl, sulfomethyl and methoxycarbonylamino.

Examples of heterocycle include unsubstituted and substituted imidazolyl, diazolyl, triazolyl, tetrazolyl, thiazolyl, thiadiazolyl, thiatriazolyl, oxazolyl, oxadiazolyl, benzimidazolyl, benzoxazolyl, benzothiazolyl, triazolylpyridyl, purinyl, pyridyl, pyrimidinyl, pyridazinyl, pyrazolyl and triazinyl.

Suitable heterocycles include unsubstituted and substituted 5-hydroxy-4-pyridon-2-yl, 1,2,3-triazolyl; 1,2,4-triazolyl; tetrazolyl; oxazolyl, thiazolyl; 1,3,4-oxadiazolyl; 1,3,4-thiadiazolyl or 1,2,3-thiadiazolyl.

Preferably the heterocycle is 1,5-dihydroxy-4-pyridon-2-yl, 5-hydroxy-1-methyl-4-pyridon-2-yl, 5-hydroxy-4-pyridon-2-yl, 1-methyl-1H-tetrazol-5-yl,2-methyl-1,3-4-thiadiazol-5-yl, 1-carboxymethyl-1H-tetrazol-5-yl, 6-hydroxy-2-methyl-5-oxo-2H-1,2,4-triazin-3-yl, 1,2,3-triazol-5-yl, 4-methyl-thiazol-5-yl.

Except where otherwise indicated organic radicals contain preferably up to 10 carbon atoms and lower refers to up to 4 carbon atoms.

Examples of acid addition salts are salts of inorganic or organic acids, e.g. hydroiodide or hydrochloride.

A particular preferred group of compounds of formula I comprise those of formula I'

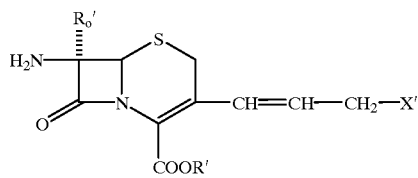

wherein R' is hydrogen or a negative charge, $R_o'$ is hydrogen, and X' is pyridinium, 1,2,3-triazol-5-ylthio or carbamoylmethylethylmethylammonium and their acid addition salts.

The compounds of formula I are known. They are characterized by their excellent spectrum of activity: for example, in EP A 333 154 and EP A 264 091, a number of compounds having a substituted ammonium-propenyl group and substituted pyridinium-propenyl group are described. EP 315 518 claims compounds of the type having isomeric thienopyridinium-propenyl derivatives. DE 3 404 615 and DE 3 512 225 describe pyridinium- and ammonium-propenyl derivatives which are substituted in the same way. U.S. Pat. No. 4,139,618 describes for example cephalosporin derivatives having thia- or oxadiazol-5-yl-thio groups as substituents.

However, according to methods known from literature, the compounds of formula I can only be produced via several intermediate steps, using extensive protecting group technology. For example, in EP 333 154, 7-β-(2-phenylacetamido)-3-chloromethylcephem-4-carboxylic acid-p-methoxybenzylester is converted into the vinylogous chloromethyl compound via the analogous iodomethyl compound, phosphonium salt and Wittig reaction with chloroacetaldehyde. The resultant compound is then reacted with a N-nucleophile according to choice, the protecting groups in position 7 and 4 are cleaved in any order and subsequently reacylated with the side chain that is applicable for the respective active substance in position 7. In another reaction sequence, for example, in the first stage the phenylacetyl protecting group at the vinylogous chloromethyl compound is cleaved, then the N-nucleophile is introduced, subsequently the ester protecting group is removed and reacylated or synthesis to form the active substance is effected in reverse order. The disadvantages of this synthesis are on the one hand the high number of stages of synthesis due to extensive protecting group technology, and on the other hand to form the vinylogous compound it is necessary to work with poisonous choroacetaldehyde which is only obtainable with extreme difficulty and with high loss in dry, monomeric form.

Another synthesis strategy is described for example in EP 315 518. Here, 7-amino-3-chloromethylcephem-4-carboxylic acid benzhydryl ester is acylated with the protected active substance side chain, subsequently vinylized again with chloracetaldehyde by means of the corresponding phosphonium salt, chloride is exchanged for iodide, reacted with the corresponding N-heterocycle and the protecting group is subsequently cleaved. Again due to extensive protecting group technology, this synthesis requires a large number of stages of synthesis with some expensive chromatography steps.

Another approach is illustrated by the synthesis method claimed in DE 3 404 615. Here, in reverse order, a Wittig reaction is carried out between a protected 7-acylamino-3-formyl-4-carboxylic acid ester with the corresponding substituted phosphoniumylide. Again, the expensive protecting group technology and the poor accessibility of the corresponding 3-formylcephem compound and of the Wittig reagent are distinct disadvantages of this synthesis.

In U.S. Pat. No. 4 139 618, in an expensive synthesis via a 3-formyl-Δ2-cephem-4-carboxylic acid ester, a Grignard reaction and sigmatropic rearrangement, 7-acylamino-3-acetoxypropenyl-cephem-4-carboxylic acid ester is produced, the ester group cleaved and the exchange with a heterocyclic thiole effected in aqueous solution. As an alternative to this, the heterocyclic thiole is introduced under acidic catalysis to a 1-hydroxypropenyl-Δ2-cephemcarboxylic acid ester. The Δ2-double bond is subsequently isomerized and the ester protecting group cleaved. One disadvantage of this process is the fact that exchange of the substituent in an aqueous medium in β-lactam chemistry is linked with considerable decomposition. In an alternative process, the product must be purified by chromatography.

In view of the many advantages of 3-substituted propenyl cephalosporines, there was still a need for a commercially useful process which provides intermediates from which a wide variety of 3-substituted propenyl cephalosporines can be produced. It is an object of this invention to provide an improved process for the production of compounds of formula I. It is a further object of this invention to provide certain new intermediates.

According to one aspect, the present invention provides a new process for the production of compounds of formula I as defined above, which comprises the step of i) subjecting a compound of formula IX

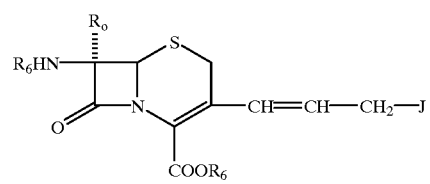

wherein $R_o$ is as defined above and $R_6$ is a silyl protecting group, to a nucleophilic exchange in 3'-position, and optionally splitting off silyl protecting groups.

Examples of silyl protecting groups include trimethylsilyl, triethylsilyl, tri-n-propyl-silyl, tri-n-butylsilyl, methyldiethylsilyl, dimethylethylsilyl, phenyldimethylsilyl, tert. butyldiphenylsilyl, tert. butyldimethylsilyl and triphenylsilyl. The trimethylsilyl group is preferred.

The exchange reaction with a nucleophile, according to the invention, is extremely simple. By adding the corresponding N-nucleophile as a free base or in the form of an anion, a compound of formula IX is converted into the N,O-bissilylated derivative of formula I, i.e. wherein R and R$_1$ are silyl protecting groups, which groups may be splitt off by simple hydrolysis or alcoholysis to give compounds of formula I, wherein R is hydrogen or a negative charge and R$_1$ is hydrogen.

The compounds having substitution type d) are obtained whereby the corresponding amine is reacted in the form of a Schiff base and the aldehyde component is removed in known manner when the reaction with the compound of formula IX has taken place.

In the same way, the reaction with S-heterocycles is simple. The compounds of formula I are obtained by adding the S-heterocycle in the form of its alkali or alkaline earth salt, in the form of a quaternary ammonium salt or in the form of the free mercapto compound, in the presence of an acid trap, with subsequent hydrolysis or alcoholysis of the silyl protecting groups. If desired, in order to raise the solubility of the heterocycle in the reaction system, a cosolvent such as an organic amide, a urea or a polar carbonyl derivative, is added.

If readily silylable functions are contained in the nucleophiles as substituents, these are optionally silylated with one of the silylation agents mentioned below in step iii) prior to the reaction with a compound of formula IX.

The compounds of formula I can be isolated in conventional manner. Silyl protecting groups may be removed by simple hydrolysis or alcoholysis. This may be effected e.g. either by adding a desilylation agent to the reaction mixture, or the product is extracted into a separable aqueous phase, by adding water either under alkaline or acidic conditions and precipitating by adjusting the pH value to the isoelectric point, optionally adding an organic solvent.

The compounds of formula IX are new and also form part of the invention.

The compounds of formula IX, as well as of formula I, VII and VIII, include two isomers, namely (E)-isomer (i.e. a trans-isomer) and (Z)-isomer (i.e. a cis-isomer) and a mixture thereof.

A compound of formula IX is conveniently obtained by the step of ii) reacting a compound of formula VIII

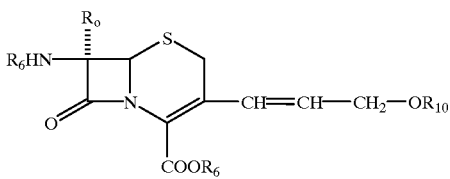

wherein R$_o$ and R$_6$ are defined as above, and R$_{10}$ is a silyl protecting group, an optionally substituted straight or branched alkyl radical, an optionally substituted aryl or acyl radical, with an iodinating agent.

Examples of aryl in the definition of R$_{10}$ include phenyl or naphthyl, optionally substituted with up to 3 groups selected from halogen, (C$_{1-4}$)alkyl or (C$_{1-4}$)alkoxy. Examples of acyl are (C$_{1-4}$)alkylcarbonyl e.g. formyl or acetyl, or benzoyl.

Suitable solvents are inert, organic solvents, e.g. halogenated hydrocarbons, such as dichloromethane or chloroform, inert nitriles such as acetonitrile or sulfolane.

Suitable iodinating agents for the production of a compound of formula IX are trialkyliodosilanes, for example trimethyliodosilane or diiodosilane. The iodinating agent may be employed in a stoichiometric quantity or in excess.

The temperature during iodination depends on the reactivity of the oxygen derivative in formula VIII. Thus, temperatures of −50° C. to boiling point of the reaction mixture are possible. It is preferable to operate at a temperature of −20° C. to +20° C.

During the iodination reaction, the compound of formula IX is surprisingly obtained predominantly as the E-isomer; after longer reaction times or on addition of an inert polar solvent, e.g. acetonitrile or sulfolane, practically exclusively E-isomers are formed. Thus in the subsequent products of formula I, the E-configuration on the double bond also dominates.

A compound of formula VIII is conveniently obtained by iii) silylating a compound of formula VII

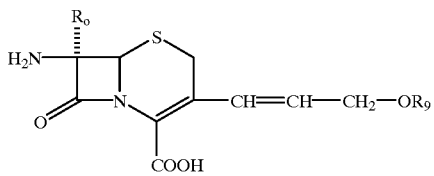

wherein R$_o$ is defined as above and R$_9$ is hydrogen, an optionally substituted straight or branched alkyl radical, an optionally substituted aryl radical or an acyl radical.

Suitable silylation agents are strong silylation agents, such as hexamethyldisilazane, in the presence of a catalyst, e.g. an organic acid, a quaternary ammonium salt or a mixture of hexamethyldisilazane with a silylation agent such as trimethylchlorosilane or trimethyliodosilane. In the same way, silylation agents such as bis-trimethylsilyl-trifluoroacetamide or bissilylurea may be used in combination with one of the above-mentioned silylation agents. Suitable solvents are inert organic solvents, e.g. halogenated hydrocarbons, such as dichloromethane or chloroform, inert nitrites such as acetonitrile, or acyclic or cyclic ethers. It is preferable to use the solvents which in the next stage are inert towards the iodinating agent. Solvents which are not inert have to be removed and replaced prior to the reaction with the iodinating agent. The temperature for the silylation reaction is not critical, and may be up to boiling point of the relevant solvent.

The compounds of formula VII may be employed in any E:Z ratio.

The compounds of formula VIII may then be reacted in situ with an iodinating agent to form compounds of formula IX, which may then be subjected in situ to a nucleophilic exchange in 3'-position to give compounds of formula I.

The compounds or formula VII may be prepared in known manner. For example they may be prepared by the method described in European Patent Application No. 92103666.1 by reacting a 7-silylated-3-iodomethyl-3-cephem-4-carboxylic acid silyl ester (obtainable from e.g. 7-ACA) with e.g. triphenylphosphine to give a 7-silylated-3-triphenylphosphoniummethyl-3-cephem-4-carboxylic acid silyl ester which is reacted with a base and then with an aldehyde to give compounds of formula VII.

The process according to the invention, compared with the state of the art, has the simplest protecting group technology, is a one-pot reaction and is effected under mild, aprotic conditions. It may be used on industrial scale. The reaction steps i), ii), and iii) are preferably carried out in a one-pot process without isolation of the intermediates. The process uses silyl groups as protecting groups, which may be introduced in a single step and also may be cleaved in one single step, thus reducing the number of steps. Silyl protecting groups may be removed by simple hydrolysis or alcoholysis at the end of the reaction.

The relevant products may be obtained in pure form by reprecipitation, resp. recrystallization, without any chromatography steps. In its preliminary stages of vinylization of 7-aminocephalosporanic acid in the Wittig stage, the process according to the invention enables work to be effected using ecologically acceptable and safe aldehydes. The new compound of formula IX is a central intermediate product for the production of compounds of formula I. In addition, this method of synthesis leaves open the option of subsequently adding an acyl radical in position 7 without expensive protecting group technology.

The compounds of formula I are important starting products in the production of valuable cephalosporin antibiotics. Cephalosporins which are propenyl-substituted in 3-position are either resorbed orally, or when applied parenterally, they are characterized for their very broad efficient spectrum of activity. For example, the following compound 2 g of 7-amino-3-(3-formyloxy-1-propen-1-yl)-3-cephem-4-carboxylic acid are suspended in 40 ml of dichloromethane. After adding 0.16 g of saccharin and 5.3 ml of hexamethyldisilazane, the reaction mixture is boiled at reflux for 5 hours under a light current of $N_2$. The title compound is again examined by NMR spectroscopy after evaporating the dichloromethane and taking up the residue in $CDCl_3$.

b) 7-Trimethylsilylamino-3-(3-iodo-1-propen-1-yl)-3-cephem-4-carboxylic acid trimethylsilyl ester, E-isomer (compound of formula IX)

2.5 ml of iodotrimethylsilane are added at 0° to the solution of 7-trimethylsilylamino-3-(3-formyloxy-1-propen-1-yl)-3-cephem-4-carboxylic acid trimethylsilyl ester obtained in Example 2a) in dichloromethane, and the solution is stirred for 4½ hours at 0°. The NMR-spectroscopic data are identical to the data given in Example 1.

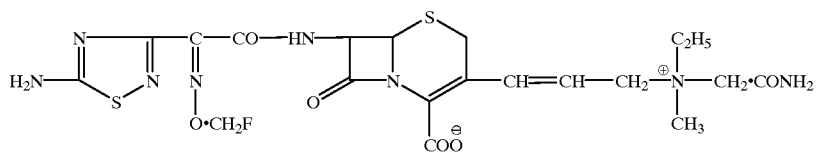

may be produced.

In the following examples, which illustrate the invention more fully, but in no way limit its scope, all temperatures are given in degrees celsius.

EXAMPLE 1

7-Trimethylsilylamino-3-(3-iodo-1-propen-1-yl)-3-cephem-4-carboxylic Acid Trimethylsilyl Ester, E-isomer (Compound of Formula IX)

a) 7-Trimethylsilylamino-3-(3-acetoxy-1-propen-1-yl)-3-cephem-4-carboxylic acid trimethylsilyl ester (compound of formula VIII)

596.6 mg of 7-amino-3-(3-acetoxy-1-propen-1-yl)-3-cephem-4-carboxylic acid are suspended in 7.2 ml of absolute dichloromethane. 29.4 mg of saccharin are added, followed by 1.04 ml of hexamethyldisilazane. The resultant solution is boiled at reflux for 20 hours under a light current of $N_2$. Due to the extreme hydrolyzability, characterization is effected by NMR.

b) 7-Trimethylsilylamino-3-(3-iodo-1-propen-1-yl)-3-cephem-4-carboxylic acid trimethylsilyl ester, E-isomer (compound of formula IX)

0.71 ml of iodotrimethylsilane are added at 0° to the solution, produced as described under a), of 7-trimethylsilylamino-3-(3-acetoxy-1-propen-1-yl)-3-cephem-4-carboxylic acid trimethylsilyl ester. The solution is stirred for 15 hours at 0°. Due to the extreme hydrolyzability, characterization is again effected by NMR.

EXAMPLE 2

7-Trimethylsilylamino-3-(3-iodo-1-propen-1-yl)-3-cephem-4-carboxylic Acid Trimethylsilyl Ester, E-isomer (Compound Formula IX)

a) 7-Trimethylsilylamino-3-(3-formyloxy-1-propen-1-yl)-3-cephem-4-carboxylic acid trimethylsilyl ester (compound of formula VIII)

EXAMPLE 3

7-Trimethylsilylamino-3-(3-iodo-1-propen-1-yl)-3-cephem-4-carboxylic acid trimethylsilyl ester, E-isomer (compound of formula IX)

a) 5.25 g of 7-amino-3-(3-acetoxy-1-propen-1-yl)-3-cephem-4-carboxylic acid are bisilylated in dichloromethane analogously to the manner described in Example 1a.

b) 5 g of diiodosilane are added at 0° to the solution of 7-tri- methylsilylamino-3-(3-acetoxy-1-propen-1-yl)-3-cephem-4-carboxylic acid obtained in Example 3a), and the solution stirred for 7 hours at 0°. HPLC shows the typical peaks (desilylated title compound and reaction products with HPLC solvent) of the title compound.

HPLC conditions:

Sample preparation: 0.1 ml of reaction solution per 50 ml of $H_2O$ +$NaHCO_3$

Stationary phase: nucleosil $Rp_{18}$ 10 μm, 200×4.7 mm, flow 1 ml/min, λ=256 nm Mobile phase: 0.02 m pentanesulphonic acid-Na in $H_2O$ Amount injected: 20 μl HPLC sample solution Retention times: 1.79, 2.77, 4.22 min.

EXAMPLE 4

7-Amino-3-[(E)-3-(carbamoylmethylethylmethylammonium)-1-propen-1-yl]-3-cephem-4-carboxylic Acid Iodide (Compound of Formula I)

A solution of 35.9 g of 7-trimethylsilylamino-3-(3-iodo-1-propen-1-yl)-3-cephem-4-carboxylic acid trimethylsilyl ester, produced from 21 g of 7-amino-3-(3-acetoxy-1-propen-1-yl)-3-cephem-4-carboxylic acid analogously to the manner described in example 1a), in ca. 210 ml of dichloromethane is mixed at 0° with a solution, which has been boiled for 2 hours, of 29.4 g of N-methyl,N-ethyl-glycine-amide, 40.9 g of hexamethyldisilazane and 3.7 g of saccharin in 200 ml of acetonitrile. The mixture is stirred for 4 hours at 0°. Subsequently, ca. 200 ml of isopropanol are added, whereby the title compound precipitates as a raw product. It is isolated through a suction filter, washed with isopropanol and subsequently dried in a vacuum drying chamber. The raw product is dissolved and reprecipitated by adding aqueous hydrochloric acid, treated with carbon and precipitated with isopropanol at pH=2.5 to yield the pure title compound as a slightly yellowish, crystalline powder.

EXAMPLE 5

7-Amino-3-[(E)-3-pyridinium-1-propen-1-yl)-3-cephem-4-carboxylic Acid Iodide (Compound of Formula I)

A solution of 25.7 g of 7-trimethylsilylamino-3-(3-iodo-1-propen-1-yl)-3-cephem-4-carboxylic acid trimethylsilyl ester, produced from 15 g of 7-amino-3-(3-acetoxy-1-propen-1-yl)-3-cephem-4-carboxylic acid analogously to the manner described in Example 1, in 150 ml of dichloromethane is mixed at 0° with 14.6 ml of dry pyridine, and the reaction mixture is stirred over night at 0°. Subsequently, 150 ml of isopropanol are added, whereby the title compound precipitates as the raw product. The raw product is isolated through a suction filter, washed with isopropanol and dried in a vacuum drying chamber. By dissolving the raw product in methanol/aqueous hydrochloric acid, carbonizing and readjusting the pH value with triethylamine to ca. pH 3, the pure title compound is obtained as a practically colourless powder.

EXAMPLE 6

7-Amino-3-[(E)-3-(1,2,3-triazol-5-ylthio)-1-propen-1-yl]-3-cephem-4-carboxylic Acid (Compound of Formula I)

A solution of 25.7 g of trimethylsilylamino-3-(3-iodo-1-propen-1-yl)-3-cephem-4-carboxylic acid trimethylsilyl ester, produced from 15 g of 7-amino-3-(3-acetoxy-1-propen-1-yl)-3-cephem-4-carboxylic acid analogously to the manner described in Example 1, in 300 ml of dichloromethane is mixed at 0° with a solution of 12.4 g of 5-mercapto-1,2,3-triazole-Na salt in 25 ml of dry dimethylformamide. The reaction mixture is stirred over night at 0° and 300 ml of isopropanol are subsequently added. The title compound precipitates as a filterable raw product. This is washed with isopropanol and dried in a vacuum drying chamber. By dissolving the raw product in water with HCl, treating with carbon and correcting the pH to ca. 3, the title compound is obtained as a crystalline, almost white powder.

$^1$H-NMR-SPECTRA

Ex: Spectrum:

1a (CD$_2$Cl$_2$) 7.06 (d, J=17.4 Hz, 3-CH=, E-isomer); 6.31 (d, J=11.3 Hz, 3-CH=, Z-isomer); 6.02–5.93 (m, C=CH—CH$_2$—, E-isomer); 5.70–5.60 (m, C=CH—CH$_2$—, Z-isomer); 4.98 (d, J=5.2 Hz, H$_6$, E-isomer); 4.93 (d, J=5.2 Hz, H$_6$, Z-isomer); 4.76 (dd, J=5.2 Hz, J=13.1 Hz, H$_7$, E- and Z-isomer); 4.65–4.38 (m, CH$_2$—O—); 3.58 (AB, J=17.4 Hz, S—CH$_2$, E-isomer); 3.42 (AB, J=18.3 Hz, S—CH$_2$, Z-isomer); 2.04 (s, CH$_3$, E-isomer); 1.99 (s, CH$_3$, Z-isomer); 1.49 (d, J=13.1 Hz, N—H); 0.311 (s, COOSi—CH$_3$, E-isomer); 0.273 (s, COOSi—CH$_3$, Z-isomer); 0.087 (s, NH—Si—CH$_3$, E- and Z-isomer).

1b/2b (CD$_2$Cl$_2$) 7.07 (d, J=15.7 Hz, 3-CH=); 6.15 (dt, J=15.7 Hz, J=7.9 Hz, =CH—CH$_2$-J); 4.87 (d, J=5.2 Hz, H$_6$); 4.75 (dd, J=5.2 Hz, J=13.1 Hz, H$_7$); 4.06 (d, J=7.9 Hz, CH$_2$-J); 3.57 (AB, J=17.4 Hz, S—CH$_2$); 1.50 (d, J=13.1 Hz, NH)

2a (CDCl$_3$) 8.14 (s, HC=O, E-isomer); 8.08 (s, HC=O, Z-isomer); 7.26 (d, J=16.5 Hz, 3-CH=, E-isomer); 6.44 (d, J=11.7 Hz, 3-CH=, Z-isomer); 6.17–5.59 (m, C=CH—CH$_2$, E- and Z-isomer); 4.96 (d, J=4.5 Hz, H$_6$); 4.82 (dd, J=13.5 Hz, J=4.5 Hz, H$_7$); 4.80–4.44 (m, —CH$_2$—O); 3.48 (AB, J=18.3 Hz, S—CH$_2$, Z-isomer); 3.62 (AB, S—CH$_2$, E-isomer); 1.46 (d, J=13.5 Hz, NH); 0.56 (s, COO—SiCH$_3$, E-isomer); 0.39 (s, COOSiCH$_3$, Z-isomer); 0.18 (s, NH—Si—CH$_3$, E- and Z-isomer).

4 (D$_2$O) 6.84 (d, J=15.7 Hz, CH=); 5.87 (dt, J=15.7 Hz, J=7.6 Hz, =CH—CH$_2$—); 5.23 (d, J=5.1 Hz, H$_6$); 5.07 (d, J=5.1 Hz, H$_7$); 4.21–4.08 (m, =CH—CH$_2$—N+); 3.96 (b, +N—CH$_2$—C=O); 3.68 (AB, J=17.4 Hz, S—CH$_2$—); 3.58–3.42 (m, CH$_2$—CH$_3$, diastereoisomers); 3.09 and 3.08 (s, S, +N—CH$_3$, diastereoisomers); 1.29 (t, J=7.2 Hz, CH$_2$—CH$_3$).

5 (D$_2$O/DCl) 8.94–8.03 (m, Py—H); 7.14 (d, J=16.2 Hz, 3—CH=); 6.40 (dt, J=16.2 Hz, J=6.5 Hz, =CH—CH$_2$); 5.38 (d, J=6.5 Hz, CH$_2$—Py); 5.34 (d, J=5 Hz, H$_7$); 5.18 (d, J=5 Hz, H$_6$); 3.84 (b, S—CH$_2$—).

6 (CF$_3$COOD) 8.48 (s, triazole-H); 7.34 (d, J=16.2 Hz, 3-CH=); 6.46 (dt, J=16.2 Hz, J=7.5 Hz); 5.51 (d, J=3.8 Hz, H$_7$); 5.38 (d, J=3.8 Hz, H$_6$); 3.93 (d, J=7.5 Hz, CH$_2$—S—, triazole); 3.81 (b, S—CH$_2$—).

What is claimed is:

1. A process for the production of a 7-acylamino-3-(propen-1-yl)-3-cephem-4-carboxylic acid wherein the propen-1-yl group in position 3 of the ring structure is substituted in position 3' by a residue of a nucleophile, X, which process comprises:

(a) reacting a compound of formula IX

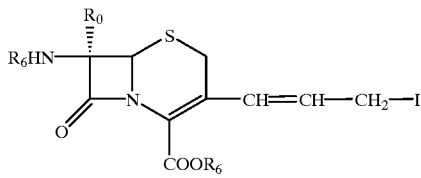

wherein

R$_o$ is hydrogen or methoxy and

R$_6$ is a silyl protecting group which is trimethylsilyl, triethylsilyl, tri-n-propyl-silyl, tri-n-butylsilyl, methyldiethylsilyl, dimethylethylsilyl, phenyldimethylsilyl, tert-butyldiphenylsilyl, tert-butyldimethylsilyl or triphenylsilyl, with a reactant form of the nucleophile radical X to obtain a compound of formula IX wherein the iodine group is replaced by the residue of the nucleophile X, wherein the nucleophile radical X is (1)

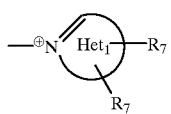

wherein Het₁ is a 5- or 6-membered heterocycle which may contain one or two additional heteroatoms selected from oxygen, nitrogen or sulphur atoms, $R_7$ is hydrogen, carboxy, carboxamido, a sulphonic acid radical, alkoxy, hydroxy, acyl, amino, alkylthio, mercapto, or both the $R_7$'s are a saturated or unsaturated alkyl group, or form part of a saturated or unsaturated carbocyclic ring;

(2) an aliphatic ammonium group of formula III

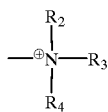

wherein $R_2$, $R_3$ and $R_4$ may be the same or different and are respectively alkyl, alkenyl, aryl, hydroxy lower alkyl, carbamoyl lower alkyl, amino lower alkyl, acylamino lower alkyl, cyano lower alkyl, carboxy lower alkyl or oxopropyl, or $R_2$ with $R_3$ and the nitrogen atom form a carbocyclic unsaturated ring which is alkyl-substituted by $R_4$ in which $R_4$ may additionally represent a 1,3- or 1,4-alkylene or vinylene bridge or $R_2$ and $R_3$ and the nitrogen atom form a carbocyclic saturated ring, wherein $R_4$ is a vinylene bridge;

(3) a saturated heterocyclic ammonium group which is 1-methylpyrrolidinium, pyrrolidinium, piperidinium, 1-methylpiperidinium, 1-methylpiperazinium, 1-methylpyrazolidinium, 1,5-diazabicyclo[3.3.0]octan-1-ium, 1,4-diazabicyclo[2.2.2]octan-1-ium, quinuclidinium or 1-aza-5-methyl-4,6-dioxabicyclo[3.3.1]nonan-1-ium;

(4) a nitrogen base of formula IV

wherein $R_5$ is hydrogen or has the significance of $R_2$ above;

(5) a tetrazole, triazole, imidazole, pyrrolidine or pyrazole group;

(6) a heterocyclic thio radical of formula V

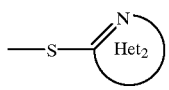

wherein Het₂ is
(i) 1,5-dihydroxy-4-pyridon-2-yl,
(ii) 5-hydroxy-1-methyl-4-pyridon-2-yl,
(iii) 5-hydroxy-4-pyridon-2-yl,
(iv) 1-methyl-1H-tetrazol-5-yl,
(v) 2-methyl-1,3,4-thiadiazol-5-yl,
(vi) 1-carboxymethyl-1H-tetrazol-5-yl,
(vii) 6-hydroxy-2-methyl-5-oxo-2H-1,2,4-triazin-3-yl, 1,2,3-triazol-5-yl, or
(viii) 4-methylthiazol-5-yl;

(7) a thio radical of formula VI

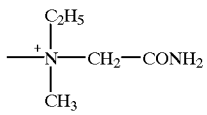

in which $R_8$ is alkyl, alkenyl, aryl, acyl, carbamoyl, thiocarbamoyl or carbalkoxy radical or a thio-analog thereof; or (8) $N_3$;

and which process further comprises
(b) acylating the amine group in position 7 with an acylating agent.

2. A process of claim 1 further comprising splitting off the silyl protecting groups by hydrolysis or alcoholysis.

3. A process according to claim 1 for the production of a 7-acylamino-3-(propen-1-yl)-3-cephem-4-carboxylic acid wherein the propen-1-yl group in position 3 of the ring structure is substituted in position 3' by a residue of a nucleophile X of the formula

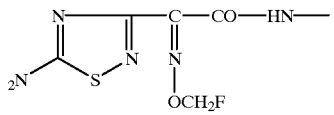

and wherein the amine group in position 7 is substituted by an acyl group of the formula

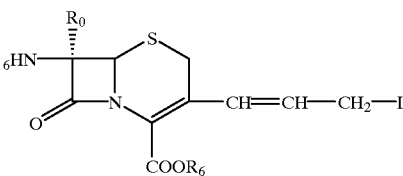

which process comprises:
a) reacting a compound of formula IX

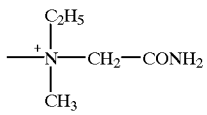

IX with a reactant form of the nucleophile radical, X, to obtain a compound of formula IX wherein the iodine group is replaced by the residue of a nucleophile X, and
b) acylating the amine group in position 7 with a reactive form of the acyl group.

* * * * *

UNITED STATES PATENT AND TRADEMARK OFFICE
CERTIFICATE OF CORRECTION

PATENT NO.    : 6,169,180 B1					Page 1 of 1
DATED         : January 2, 2001
INVENTOR(S)   : Ludescher et al.

It is certified that error appears in the above-identified patent and that said Letters Patent is hereby corrected as shown below:

<u>Title page,</u>
Left column, section [30] under Foreign Application Priority Data should read:
August 21, 1991 [AT]        A1636/91

Signed and Sealed this

Eleventh Day of September, 2001

*Attest:*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO. : 6,169,180 B1
DATED : January 2, 2001
INVENTOR(S) : Ludescher et al.

It is certified that error appears in the above-identified patent and that said Letters Patent is hereby corrected as shown below:

<u>Title page, left column,</u>
Item [30] under Foreign Application Priority Data should read --
August 21, 1991 (AT) 07/932,145 --

Signed and Sealed this

Thirtieth Day of October, 2001

Attest:

*Attesting Officer*

NICHOLAS P. GODICI
*Acting Director of the United States Patent and Trademark Office*